(12) United States Patent
Wakabayashi et al.

(10) Patent No.: US 6,645,996 B1
(45) Date of Patent: Nov. 11, 2003

(54) PHYSIOLOGICALLY ACTIVE SUBSTANCES

(75) Inventors: Toshiaki Wakabayashi, Ibaraki (JP); Rena Kawase, Ibaraki (JP); Nobuaki Naruse, Ushiku (JP); Masanori Fujita, Ibaraki (JP); Tomohiro Sameshima, Kanagawa (JP); Yoshio Watanabe, Kanagawa (JP); Kazuyuki Dobashi, Kanagawa (JP); Yasuhiro Funahashi, Ibaraki (JP); Taro Semba, Ibaraki (JP)

(73) Assignee: Mercian Corporation and Eisai Co., Ltd., Tokyo (JP)

(*) Notice: Subject to any disclaimer, the term of this patent is extended or adjusted under 35 U.S.C. 154(b) by 0 days.

(21) Appl. No.: 09/700,680

(22) PCT Filed: Apr. 28, 1999

(86) PCT No.: PCT/JP99/02288

§ 371 (c)(1),
(2), (4) Date: Nov. 17, 2000

(87) PCT Pub. No.: WO99/60000

PCT Pub. Date: Nov. 25, 1999

(30) Foreign Application Priority Data

May 18, 1998 (JP) .............................. 10/135205

(51) Int. Cl.$^7$ .................. A61K 31/35; C07D 305/14
(52) U.S. Cl. ............................ 514/451; 549/332
(58) Field of Search ................... 514/460, 451; 549/332

(56) References Cited

FOREIGN PATENT DOCUMENTS

| JP | 62-28144 | * 12/1987 |
| JP | 62-294619 | * 12/1987 |
| JP | 63-22583 | * 1/1988 |

(List continued on next page.)

OTHER PUBLICATIONS

The Journal of Biologicsl Chemistry, vol. 267, No. 16, Issue of Jun. 5, PP. 10931–10934, 1992.

(List continued on next page.)

*Primary Examiner*—Alan L. Rotman
*Assistant Examiner*—Binta Robinson
(74) *Attorney, Agent, or Firm*—Birch, Stewart, Kolasch & Birch, LLP (57) ABSTRACT

The present invention provides a novel bioactive substance having an antiangiogenic effect.

The chemical compound represented by the formula (1)

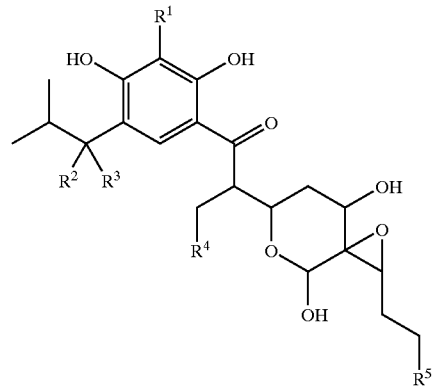

(1)

(wherein, $R^1$ represents hydrogen atom, aldehyde group or a lower acyl group, $R^2$ and $R^3$ are the same as or different from each other and represent hydrogen atom or a lower alkoxy group or are combined to represent oxygen atom, $R^4$ represents a lower alkyl group and $R^5$ represents hydrogen atom or a lower alkyl group, provided that compounds in which $R^1$ is aldehyde group, $R^2$ and $R^3$ are different from each other and are hydrogen atom or methoxy group, $R^4$ is ethyl group and $R^5$ is hydrogen atom are excluded), a salt thereof or a hydrate thereof was isolated from the culture broth of genus Streptomyces and the structure thereof was analyzed.

2 Claims, 2 Drawing Sheets

FOREIGN PATENT DOCUMENTS

| JP | 63-48213 | * | 2/1988 |
|---|---|---|---|
| JP | 63048213 A | * | 2/1988 |
| JP | 63048213 | * | 2/1988 |
| JP | 3-2148 | | 1/1991 |
| JP | 3-109324 | | 5/1991 |
| JP | 3-236324 | | 10/1991 |
| JP | 6-228144 | | 8/1994 |

OTHER PUBLICATIONS

Seminars in Medicine of the Beth Israel Hospital, Boston, vol. 333, No. 26, pp. 1757–1763, Dec. 28, 1995.

Journal ot the National Cancer Institute, vol. 82, No. 1, Jan. 3, 1990, pp. 4–6.

"Angiogenesis Inhibition Suppresses Collagen Arthritis" vol. 175, Apr. 1992 1135–1138.

The New England Journal of Medicine, vol. 320, No. 18, May 4, 1989, pp. 1197–1200.

FEBS Letters, vol. 358 (1995) pp. 311–315.

American Journal of Pathology, vol. 146, No. 5, May 1995, pp. 1029–1039.

AIDS, Proceeding of ASCO, vol. 12, Mar. 1993 p. 50.

* cited by examiner

PHYSIOLOGICALLY ACTIVE SUBSTANCES

This application is the national phase under 35 U.S.C. § 371 of PCT International Application No. PCT/JP99/02288 which has an International filing date of Apr. 28, 1999, which designated the United States of America.

FIELD OF INDUSTRIAL APPLICATION

The present invention relates to a novel bioactive substance which is effective in the prevention or treatment of various diseases accompanied by abnormal angiogenesis.

PRIOR ART

Angiogenesis is a biological phenomenon which is essential for the formation of a vascular arbor during fetal period and is also essential in the morphological and functional development of each organ. Newly blood vessels are constructed by way of plural processes such as the migration and proliferation of endothelial cells and tube formation. It is reported that in these processes, the participation of mast cells, lymph corpuscles, interstitial cells and others play an important role (J. Folkman and Y. Shing, J. Biol. Chem., 267, 10931, 1992). In adult, the angiogenesis occurs only in the female menstrual cycle and a morbid increase of angiogenesis is involved in various diseases and their progression. Given as specific examples of diseases accompanied by abnormal angiogenesis are cancers, rheumatic arthritis, atherosclerosis, diabetic retinopathy, hemangioma and psoriasis (J. Folkman, N. Engl. J. Med., 333, 1757, 1995).

It is reported that the growth of, particularly, solid cancers depends upon the angiogenesis and an antiangiogenic agent is expected to be a new chemotherapy for intractable solid cancers (Folkman J., J. Natl. Cancer Inst., 82, 4, 1990).

In the case of the rheumatic arthritis, it is reported that over production of angiogenesis factors from infiltrated macrophage/lymphatic cells leads to the induction of angiogenesis in the segments (Kahn J., Proc. Am. Soc. Clin. Oncol., 12, 50, abstract, 1993) and that an antiangiogenic agent AGM-470 inhibits arthritis in a collagen arthritis model (Peacock D J., J. Exp. Med. 175, 1135–8, 1992). These reports suggest that the inhibition of angiogenesis in inflammatory diseases results in the therapy for the diseases.

In the atherosclerosis, it is clarified that excess production of a vascular endothelial growth factor (VEGF) induced at hypoxia causes angiogenesis in an atheromatous macula (Stavri G T., FEBS Lett., 358 , 311–5, 1995) and it is said that angiogenesis is necessary for the extension of the atheromatous macula like in the case where angiogenesis is necessary for the growth of tumors (O'Brien E R., Am. J. Pathol., 146, 1029–39, 1994). For hemangioma which is sometimes related with life or death of the newborn, curing using IFN-α2a known to have an antiangiogenic effect has been attempted (White C W., N. Engl. J. Med. 320, 1197–200, 1989) As remedies for these diseases, new antiangiogenic agents are desired eagerly.

There have been reports concerning several antiangiogenic substances so far. However, no effective substance which is fit for actual use has not been found yet (JP-A 3-109324, JP-A 3-236324 and JP-A 3-2148).

The present invention is to isolate a novel substance having an antiangiogenic effect to thereby provide an agent for preventing or treating various diseases accompanied by abnormal angiogenesis.

DISCLOSURE OF THE INVENTION

In view of the above situation, the inventors of the present invention have carried out research screening of antiangiogenic compound and as a result, found that an antiangiogenic compound is produced in a culture broth of microorganisms belonging to the genus Streptomyces. The active substance was isolated to determine the structure and as a result, it was clarified that this active substance was a novel active substance. Then the mechanism of action of the active substance was analyzed and as a result, found that this active substance had an inhibitory effect of the expression of adhesion molecule on endothelial cells as one of the mechanisms of inhibitory effects. Specifically, the substance showed a clear inhibitory effect on the expression of VCAM-1 and E-selectin of an endothelial cell. It is suggested that VCAM-1 and E-selectin are involved in the migration of endothelial cells and formation of lumens which are essential for angiogenesis (A. E. Koch et al, Nature, 376, 517, 1995). It is reported that the both are also involved in the adhesion of an endothelial cell to the lymph corpuscle. It is hence considered that the active substance is expected to be remedies for various diseases, specifically, autoimmune diseases, e.g., collagen diseases and graft rejection, cardiac infarction and arterial sclerosis, caused by an abnormal reaction of activated lymph corpuscles besides the diseases caused by an angiogenesis.

That is, the present invention relates to a chemical compound represented by the formula (1):

(wherein, $R^1$ represents hydrogen atom, aldehyde group or a lower acyl group, $R^2$ and $R^3$ are the same as or different from each other and represent hydrogen atom or a lower alkoxy group or are combined to represent an oxygen atom, $R^4$ represents a lower alkyl group and $R^5$ represents hydrogen atom or a lower alkyl group, provided that compounds in which $R^1$ is aldehyde group, $R^2$ and $R^3$ are different from each other and are hydrogen atom or methoxy group, $R^4$ is ethyl group and $R^5$ is hydrogen atom are excluded), a salt therof or a hydrate thereof.

More specifically, it relates to a compound, a salt thereof or a hydrate thereof, in which, in the formula (1) $R^1$ represents hydrogen atom, aldehyde group or acetyl group, $R^2$ and $R^3$ are the as same or different from each other and represent hydrogen atom or methoxy group or are combined to represent an oxygen atom, $R^4$ represents ethyl group, normal propyl group or isopropyl group and $R^5$ represents hydrogen atom or methyl group, provided that compounds in which $R^1$ is aldehyde group, $R^2$ and $R^3$ which are different from each other and are hydrogen atom or methoxy group, $R^4$ is ethyl group and $R^5$ is hydrogen atom are excluded;

a compound, a salt thereof or a hydrate thereof, wherein, in the formula (1), $R^1$ represents aldehyde group, $R^2$ and $R^3$ are the same as each other and represent hydrogen atoms, R⁴ represents ethyl group and R⁵ represents hydrogen atom or methyl group;

a compound, a salt thereof or a hydrate thereof, wherein, in the formula (1), R¹ represents aldehyde group, R² and R³ are the same as each other and represent hydrogen atoms, R⁴ represents normal propyl group or isopropyl group and R⁵ represents hydrogen atom;

a compound, a salt thereof or a hydrate thereof, wherein, in the formula (1), R¹ represents aldehyde group, R² and R³ are different from each other and represent hydrogen atom or methoxy group, R⁴ represents normal propyl group or isopropyl group and R⁵ represents hydrogen atom;

a compound, a salt thereof or a hydrate thereof, wherein, in the formula (1), R¹ represents hydrogen atom, R² and R³ are the same as each other and are combined to represent an oxygen atom, R⁴ represents ethyl group or isopropyl group and R⁵ represents hydrogen atom;

a compound, a salt thereof or a hydrate thereof, wherein, in the formula (1), R¹ represents acetyl group, R² and R³ are the same as each other and represent hydrogen atoms, R⁴ represents ethyl group and R⁵ represents hydrogen atom;

a medicament which comprises the above compounds or the compound in which, in the formula (1), R¹ represents aldehyde group, R² and R³ are different from each other and represent hydrogen atom or methoxy group, R⁴ represents ethyl group and R⁵ represents hydrogen atom, a salt thereof or a hydrate thereof as the active ingredient; and a method of producing the above compounds or a salt thereof, which comprises culturing Streptomyces sp. Mer-VD1207, FERM P-15889 in a nutrient medium and collecting the above compounds or a salt thereof from the culture broth.

The present invention provides a medical composition which comprises a pharmacologically effective amount of the above compounds, a salt or a hydrate thereof and a pharmacologically acceptable carrier; a method for treating a disease against which an antiangiogenic effect or an effect of inhibiting the expression of an adhesion molecules VCAM-1 or/and E-selectin is efficacious, which comprises administering a pharmacologically effective amount of the above compounds, a salt thereof or a hydrate thereof to a patient; or use of the above compounds, a salt or a hydrate thereof for manufacturing a treating agent for a disease against which an antiangiogenic effect or an effect of inhibiting the expression of an adhesion molecules VCAM-1 or/and E-selectin is efficacious.

The present invention provides an agent for preventing or treating rheumatic arthritis, solid cancers, atherosclerosis, diabetic retinopathy, hemangioma and psoriasis.

DETAILED DESCRIPTION OF THE INVENTION

As raw materials of the compound of the present invention, it is expected that any one of strains belonging to the genus Streptomyces can be used. However, as a typical strain used in the present invention, a strain which is actinomycetes separated from the soil collected in Kumamoto prefecture and was numbered as "Mer-VD1207 strain" by the inventors is exemplified. The mycological properties of this Mer-VD1207 strain were as follows.

The cultivation was all carried out at 28° C. The culture medium was selected from those recommended by International Streptomyces Project Committee (hereinafter referred to as ISP) The color tone is described by indicating the symbols shown in the parenthesis according to Color Harmony Manual of Container Corporation of America.

(1) Morphology

A microscopic inspection of the strain showed that vegetative mycelia elongated thoroughly and allowed aerial mycelia which likewise much elongated to adhere thereto. The apex of the aerial hyphae segmented into cylindrical spores. The external dimensions of the spore were 0.6–0.8 μm-diameter×0.8–1.0 μm. The surface of the spore was smooth. The spores grew into a straight pore chain in which 10 to 50 pores were chained.

(2) Growth on Various Culture Media

ISP-2 medium: The strain grew well and put forth reddish spores on poor aerial hyphae. The reverse side of colony was brown. The strain produced an yellowish brown-brown soluble pigment in the culture medium.

ISP-3 medium: The growth of the strain was not so well. And aerial mycelia were scant and white color. The reverse side colony was brown.

ISP-4 medium: The strain grew well and put forth reddish (5dc; Grayish yellowish pink) spores on rich aerial spores. The reverse side colony was yellowish brown.

ISP-5 medium: The strain grew moderately and put forth reddish spores on poor aerial hyphae. The reverse side colony was brown. The strain produced an yellowish brown-brown soluble pigment in the culture medium.

ISP-7 medium: The strain produced melanin pigment (the culture medium blacked).

The produced soluble pigments were not changed in color caused by pH.

(3) Utilization of Carbon Sources

Mycelium cake of the strain was inoculated on agar medium added each of various sugars ISP-9 and cultured for 3 to 10 days to observe its growth condition. The strain well-utilized glucose, fructose, rhamnose, sucrose, inositol, mannose, arabinose and xylose as carbon sources.

(4) Cell Wall Analysis of the Strain

Mycelium cake of the strain was hydrolyzed using 6N HCl overnight. The concentrate was isolated using cellulose TLC and compared with a standard diaminopimelic acid to confirm its isomeric type. The isomeric type of the resulting diaminopimelic acid was LL type.

It is clear from the foregoing taxonomical study that the strain of the present invention belongs to the genus Streptomyces. The inventors of the present invention deposited this strain with National Institute of Bioscience and Human-Technology Agency of Industrial Science and Technology (Postal code 305-8566, 1-1-3, Higashi, Tsukuba-shi, Ibaraki-ken, Japan) as Streptomyces sp. Mer-VD1207 numbered as FERM P-15889 on Sep. 27, 1996. The strain was also transferred as international deposit No. FERM BP-6693 on Apr. 5, 1999.

Fermentation of the Microorganism

Although a method of the cultivation of the aforementioned microorganisms conforms in principle to a method of the cultivation of ordinary microorganisms, preferably the cultivation is carried out in an aerobic condition such as those used in an aerobic stirring culture method in general.

As the culture medium used in the cultivation, any culture medium containing a nutrient which can be utilized by microorganisms belonging to the genus Streptomyces may be used. Anyone of various synthetic media, semi-synthetic media, natural media and the like maybe used. As the composition of the medium, glucose, sucrose, fructose, glycerol, dextrin, starch, molasses, corn steep liquor, organic acids may be used as a carbon source singly or in combinations of two or more. As the nitrogen source, organic nitrogen source such as a pharmamedia, peptone, meat extract, yeast extract, soybean meal, casein, amino acid and urea and inorganic nitrogen source such as sodium nitrate and ammonium sulfate may be used singly or in combinations of two or more. A sodium salt, potassium salt, magnesium salt, phosphate and other salts of heavy metals may be added and used according to the need. It is to be noted that when conspicuous foaming is observed, various known defoaming agents may be added appropriately in the medium to the extent that the addition does not adversely affect the production of an object material.

The pH of the medium is preferably in an optimum pH range, generally, in the vicinity of a neutral zone. The temperature of cultivation is kept at generally 20 to 40° C. and particularly preferably around 30° C. at which the microorganisms grow well. Culture time is designed to be 1 to 5 days in the case of liquid culturing. The aforementioned various culture conditions maybe, of course, altered optionally corresponding to the types and qualities of the microorganisms to be used and external conditions. Also, corresponding to each of the aforementioned factors, optimum conditions are selected from the above range and adjusted.

In a method of screening the antiangiogenic effect, the degree of inhibition to the formation of lumens observed when an aortic fragment of a rat is cultured in a collagen gel was selected as an indicator (Nicosia R. F., Lab. Invest., 63, 115, 1990). Also, for the purpose of analyzing the mechanism of action of the antiangiogenic effect of the resulting compound, measurements were made concerning the effect of inhibiting the growth of endothelial cells by using endothelial cells derived from the human umbilical cord vein and the effect of inhibiting the expression of an adhesion molecules on endothelial cells.

The compound of the present invention can be purified from the culture broth of the microorganism as follows. The microorganism belonging the genus Streptomyces are cultured in a usual proper culture condition, the culture broth is then filtered and then extracted by an organic solvent such as butanol or methyl isobutyl ketone. The organic solvent layer is evaporated and then extracted using methanol, followed by treatment using light petroleum to obtain a crude extract. It is then fractionated by making proper use of adsorption chromatography using a silica gel or the like, LH 20 gel chromatography, partition chromatography, thin layer chromatography, paper chromatography or the like. An active fraction is confirmed by active screening. The foregoing measures are properly combined to isolate an active substance. As a solvent used in the adsorption chromatography, an organic solvent, which is usually used, such as chloroform, methanol, acetone, hexane or toluene is used. These solvents may be used by combining two or more while the concentration of the mixture solvent is appropriately selected. As a solvent used for crystallization, for example, chloroform and hexane or chloroform and carbon tetrachloride may be used. As one of the measures, there is a method developed by M. Lumb et al. (Nature, 206, 263, 1965). The structure of the isolated compound may be analyzed by measures according to a conventional method such as elemental analysis, GC-MS, NMR and melting point.

The inventors of the present invention have found that the isolated compound has a strong antiangiogenic effect. As aforementioned, based on the fact that abnormal arterialization is observed in various diseases, it is expected to serve as a preventive agent or a remedy for the diseases such as rheumatic arthritis, solid cancers, atherosclerosis, diabetic retinopathy, hemangioma and psoriasis and is effective especially as an anticancer agent.

When this compound is administered as a remedial or preventive agent for various diseases, it may be either orally administered in the form of a tablet, powder, granule, capsule or syrup, or parenterally administered as a spray, suppository, injection, external agent or drip agent. Although the dosage quite differs depending upon the degree of symptom, age and the type of hepatic disease, it is usually administered to an adult in an amount of about 1 mg to 100 mg for one to several portions a day.

In pharmaceutical preparation, a conventional pharmaceutical carrier is used to produce a target pharmaceutical by the usual method. That is, when a solid pharmaceutical for oral administration is prepared, a filler and, as required, further a binder, disintegrator, lubricant, colorant, flavoring agent are added to the base and then the resulting product is made into a tablet, coated tablet, granule, powder, capsule or the like by the usual method. These tablet and granule may be coated properly with, for example, a glaceing or gelatin coat according to the need without any problem.

When the injection is prepared, pH regulator, buffer, stabilizer, solubilizing agent and the like are added to the base if necessary, and the resulting product is made into an subcutaneous, intramuscular or intravenous injection by the usual method.

EXAMPLES

The present invention will be explained in more detail by referring to the following Examples, though the present invention is not limited by them.

Example 1

Purifying Method 100 ml of a seed medium (2% glycerol, 2% glucose, 2% soybean powder, 0.5% yeast extract, 0.25% NaCl, 0.32% $CaCO_3$, 0.0005% $CuSO_4 \cdot 5H_2O$, 0.0005% $MnCl_2 \cdot 4H_2O$ and 0.0005% $ZnSO_4 \cdot 7H_2O$) in an Erlenmeyer flask with a volume of 500 ml was inoculated with one platinum loop portion sampled from a slant culture (ISP-2 agar medium) of the Streptomyces sp. VD1207 strain. The medium was cultured on a rotary shaker at 28° C. for 2 days to obtain a primary seed culture broth. 500 ml of a medium having the same composition as above in a 3 L Sakaguchi flask was inoculated with 5 ml of the primary seed culture broth. The medium was cultured on a reciprocating type shaker at 28° C. for 48 hours to obtain a secondary seed culture broth. 100 L of a culture medium having the same composition as above in each of two fermentation tanks having a volume of 200 L was inoculated with 1 L of the secondary seed culture broth and cultured with airation (quantity of air flow: 50 L/ml, stirring speed: 185–325 r.p.m.) performed at 28° C. for 64 hours.

All of the resulting culture broth amounting 200 L was subjected to a continuous centrifuge to separate a supernatant from mycelium cake. The supernatant was allowed to pass through Diaion HP-20 with a capacity of 20 L and washed with 60 L of 20% methanol. In succession, the extract solution was eluted with 60 L of 80% acetone and the eluate was evaporated to remove acetone. The remaining aqueous solution was extracted twice with 5 L of ethyl acetate and the ethyl acetate layer was evaporated to dryness to obtain 19 g of a crude extract.

While the mycelium cake was extracted with 100 L of methanol and the resulting methanol extract was evaporated to remove methanol. The remaining aqueous solution was extracted twice with 12 L of ethyl acetate. The resulting extract was evaporated to dryness to give 74 g of a crude extract.

The extracts from the supernatant and from the mycelium cake were combined and dissolved in a small amount of dimethyl sulfoxide. The resulting mixture was divided into two lots and each lot was subjected to a column (inside diameter: 50 mm, length: 950 mm) of YMC-GEL ODS-AM 120-S50 (manufactured by YMC Co., Ltd.) which was pre-equilibrated with a mixed solution of acetonitrile/10 mM potassium dihydrogenphosphate buffer (pH: 3.5)=(4:6). The treated product was washed with a mixed solvent having the same composition as the aforementioned, a similar mixed solvent (1:1) and a similar mixed solvent (55:45). In succession, similar mixture solvents (the ratios of the components of each mixture solvent: 6:4, 65:35 and 7:3) were used in order of descending polarity to elute. The eluate was analyzed by high performance liquid chromatography. The eluates containing each of VD1207U1, U2, A1, A2, B, C, D, E, F, F', G1, G2, G' and H (column: J'sphere ODS-H80, inside diameter: 4.6 mm, length: 75 mm, manufactured by YMC Co., Ltd., mobile phase: acetonitrile/10 mM potassium dihydrogenphosphate buffer (pH 3.5)=6:4, flow rate: 1 ml/min, detection: ultraviolet absorption at 254 nm, retention time; U1, U2: 3.7 min, A1, A2: 4.8 min, B: 5.4 min, C: 6.0 min, D: 7.0 min, E: 7.4 min, F: 8.0 min, F': 8.2 min, G1, G2: 9.4 min, G': 9.8 min, H: 10.3 min) were collected respectively. A fraction containing the U1 and U2 components, a fraction containing the A1 and A2 components, a fraction containing the B component, a fraction containing the C component, a fraction containing the D component, a fraction containing the E component, a fraction containing the F component, a fraction containing the F' component, a fraction containing G1, G2 and G' components and a fraction containing the H component were respectively obtained. Each of these fractions was extracted with ethyl acetate after acetonitrile was evaporated. The ethyl acetate layer was washed with deionized water and then evaporated to dryness.

Example 2

Purification and Analysis of Structure of VD1207U1 and U2

The fraction containing the U1 and U2 components obtained in Example 1 was dissolved in ethyl acetate, to which was then added a small amount of silica gel (Silica Gel FL100D, manufactured by Fuji Silysia Chemical Ltd.) and the solvent was evaporated. The resulting residue was subjected to a silica gel column (inside diameter: 20 mm, length: 500 mm), washed with a mixed solvent of hexane/acetone (90:10) and eluted with a similar mixed solvent (85:15). The eluates containing the U1 and U2 components respectively were mixed and the mixture was concentrated to dryness.

The resulting residue was dissolved in a small amount of dimethyl sulfoxide and then subjected to fractionating HPLC (column: J'sphere ODS-H80, inside diameter: 20 mm, length: 250 mm, manufactured by YMC Co., Ltd., mobile phase: acetonitrile/10 mM potassium dihydrogenphosphate buffer (pH 3.5)=55:45, flow rate: 12 ml/min, detection: ultraviolet absorption at 254 nm, retention time; U1: 26.2 min, U2: 27.1 min). This fractionating operation was repeated and the eluates showing each peak of the U1 and U2 components were mixed and extracted with ethyl acetate after acetonitrile was evaporated. The ethyl acetate layer was washed with deionized water and then evaporated to dryness. The resulting residue was freeze-dried to give each pure white powder of VD1207 U1 and U2 in amounts of 57 mg and 132 mg, respectively.

Analysis data of the structure of VD1207 U1

1. Color and property: white powder
2. Molecular formula: $C_{23}H_{33}O_8$
3. Mass spectrum (FAB-MS): m/z 437(M+H)$^+$
4. Specific rotation: $[\alpha]^D{}_{23}$+2.5 (c 0.1, CHCl$_3$)
5. Ultraviolet absorption spectrum:
   neutral methanol: λmax nm(ε): 257(23700), 324(3100)
   acidic methanol: λmax nm(ε) 257(25000), 324(3200)
   basic methanol: λmax nm(ε): 260(10300), 317(9700), 344(8900)
6. Infrared absorption spectrum:
   Measured in a KBr powder. Main absorptions (wave number, cm$^{-1}$) 3440, 2970, 2880, 1640, 1590, 1490, 1460, 1390, 1350, 1210, 1160, 1090, 1040, 970, 930, 900, 830, 740, 670, 590, 460, 410
7. $^1$H NMR spectrum: Spectrum $^1$H-shift (J value) measured in D-chloroform 8.39 (1H, s), 6.43 (1H, s), 4.81 (1H, brs), 4.46 (1H, ddd, 11, 10, 1.5), 4.27 (1H, ddd, 11, 6, 5), 3.30 (1H, t, 6.5), 3.51 (1H, ddd, 10, 4, 3.5), 2.32 (1H, ddd, 12, 5, 1.5), 1.54 (1H, m), 3.59 (2H, m), 1.75 (1H, m), 1.61 (1H, m), 3.59 (2H, m), 1.44 (2H, m), 1.29 (3H, m), 1.29 (3H, m), 1.30 (3H, t, 7.5), 1.06 (3H, d, 7.5), 13.21 (1H, s), 13.18 (1H, s), 2.82 (1H, d, 2.5), 1.68 (1H, d, 11),
8. $^{13}$C NMR spectrum:
   Spectrum $^{13}$C-shift measured in D-chloroform 209.1 (s), 207.5 (s), 169.7 (s), 168.7 (s), 135.6 (d), 114.9 (s), 111.9 (s), 105.1 (d), 94.0 (d), 70.2 (d), 62.5 (d), 61.9 (s), 59.8 (d), 50.0 (d), 37.3 (t), 34.9 (t), 31.2 (t), 20.6 (t), 20.6 (t) 19.7 (q), 19.1 (q), 14.2 (q), 10.4 (q),
9. Solubility:
   soluble: ethyl acetate, chloroform and dimethyl sulfoxide
   insoluble: neutral water
10. High performance liquid chromatography:
    column: J'sphere ODS-H80, inside diameter: 4.6 mm, length: 75 mm (manufactured by YMC Co., Ltd.)
    solvent: acetonitrile/10 mM potassium dihydrogenphosphate
    buffer (pH 3.5)=6:4
    flow rate: 1 mL/min
    detection wave length: Ultraviolet absorption at 254nm
    retention time: 3.7 min
11. Thin layer chromatography:
    carrier: silica gel 60 F254 (Manufactured by Merck Germany)

developing solvent: hexane/acetone (7:3)
Rf value: 0.38

Analysis data of the structure of VD1207U2
1. Color and property: white powder
2. Molecular formula: $C_{23}H_{33}O_8$
3. Mass spectrum (FAB-MS): m/z 437 (M+H)$^+$
4. Specific rotation: $[\alpha]^D_{21}$ –6.2 (c 0.1, CHCl$_3$)
5. Ultraviolet absorption spectrum:
   neutral methanol: λmax nm(ε): 257 (41700), 324 (5700)
   acidic methanol: λmax nm(ε): 257 (41900), 325 (5100)
   basic methanol: λmax nm (ε): 261 (18700), 316 (17300) 346 (16700)
6. Infrared absorption spectrum:
   Measured in a KBr powder. Main absorptions (wave number, cm$^{-1}$) 3430, 2970, 2880, 1640, 1590, 1490, 1470, 1430, 1350, 1210, 1160, 1090, 1040, 990, 970, 930, 900, 830, 760, 680, 590, 540, 460
7. $^1$H NMR spectrum:
   Spectrum $^1$H-shift (J value) measured in D-chloroform 8.42 (1H, s), 6.46 (1H, s), 5.02 (1H, d, 3), 4.41 (1H, ddd, 11, 8, 1.5) 4.22 (1H, ddd, 11, 6, 5), 3.31 (1H, t, 6.5), 3.59 (1H, ddd, 10, 4, 3.5), 2.05 (1H, ddd, 12, 5, 1.5), 1.41 (1H, dd, 11, 12), 3.55 (1H, m), 1.85 (2H, m), 1.25 (2H, m), 1.63 (2H, m), 1.29 (3H), 1.29 (3H), 0.90 (3H, d, 7.5), 1.09 (3H, d, 7.5), 13.21 (1H, s), 13.17 (1H, s), 2.59 (1H, d, 3.5), 1.51 (1H, d, 12),
8. $^{13}$C NMR spectrum:
   Spectrum $^{13}$C-shift measured in D-chloroform 208.9 (s), 206.5 (s), 169.9 (s), 169.2 (s), 135.5 (d), 114.5 (s), 112.0 (s), 105.4 (d), 94.5 (d), 69.8 (d), 62.4 (d), 61.8 (s), 59.9 (d), 49.9 (d), 37.3 (d), 34.8 (d), 32 .3 (t), 20.6 (t), 20.6 (t) 19.6 (q), 19.3 (q), 14.2 (q), 10.5 (q),
9. Solubility:
   soluble: ethyl acetate, chloroform and dimethyl sulfoxide
   insoluble: neutral water
10. High performance liquid chromatography:
    column: J'sphere ODS-H80, inside diameter: 4.6 mm, length: 75 mm, (manufactured by YMC Co., Ltd.)
    solvent: acetonitrile/10 mM potassium dihydrogenphosphate buffer (pH 3.5)=6:4
    flow rate: 1 mL/min
    detection wavelength: ultraviolet absorption at 254 nm
    retention time: 3.7 min
11. Thin layer chromatography:
    carrier: silica gel 60 F254 (manufactured by Merck Germany)
    developing solvent: hexane/acetone (7:3)
    Rf value: 0.35

Example 3

Purification and Analysis of the Structure of VD1207A1 and A2

In the fraction containing the A1 and A2 components obtained in Example 1 was dissolved and then subjected to fractionating HPLC (column: J'sphere ODS-H80, inside diameter:20 mm, length: 250 mm, manufactured by YMC Co., Ltd., mobile phase: acetonitrile/10 mM potassium dihydrogenphosphate buffer (pH 3.5)=60:40, flow rate: 10 ml/min, detection: ultraviolet absorption at 254 nm, retention time: A1 and A2: 29.4 min). This fractionating operation was repeated and the eluates showing each peak of the A1 and A2 components were mixed and extracted with ethyl acetate after acetonitrile was evaporated. The ethyl acetate layer was washed with deionized water and then evaporated to dryness.

The resulting residue was dissolved in a small amount of ethyl acetate and subjected to a thin layer chromatograph plate (silica gel 60 No. 5744, manufactured by Merck Germany) using a developing solvent (toluene:methanol=9:1) to carry out preparative thin layer chromatography. After the development was completed, each spot of the A1 and A2 components was confirmed using a UV lamp (254 nm) (Rf value; A1: 0.23, A2: 0.17) and each component was eluted using a mixed solvent of ethyl acetate/methanol (1:1), followed by evaporating to dryness. The resulting residue was freeze-dried to give each pure white powder of VD1207 A1 and A2 in amounts of 6 mg and 11 mg, respectively.

Analysis data of the structure of VD1207A1
1. Color and property: white powder
2. Molecular formula: $C_{24}H_{35}O_8$
3. Mass spectrum (FAB-MS): m/z 451 (M+H)$^+$
4. Specific rotation: $[\alpha]^D_{23}$+1.9 (c 0.1, CHCl$_3$)
5. Ultraviolet absorption spectrum:
   neutral methanol: λmax nm(ε): 257 (48900), 324 (6900)
   acidic methanol: λmax nm(ε):257 (54300), 324 (7700)
   basic methanol: λmax nm(ε):261 (22100), 317 (20700), 345 (20100)
6. Infrared absorption spectrum:
   Measured in a KBr powder. Main absorptions (wave number, cm$^{-1}$) 3440, 2960, 1640, 1590, 1490, 1470, 1390, 1350, 1210, 1160, 1090, 1030, 980, 930, 830, 740, 670, 590, 460
7. $^1$H NMR spectrum:
   Spectrum $^1$H-shift (J value) measured in D-chloroform 8.43 (1H, s), 6.44 (1H, s), 4.82 (1H, brs), 4.39 (1H, ddd, 11.5, 9.5, 2), 4.27 (1H, ddd, 12, 11.5, 5), 3.30 (1H, dd, 7, 6), 3.58 (1H, m), 1.84 (1H, ddd, 13.5, 11, 4), 1.33 (1H, ddd, 13.5, 10, 3.5), 2.34 (1H, ddd, 12, 5, 2), 1.53 (1H, ddd, 12, 12, 11.5), 3.59 (1H, sept, 7), 1.44 (1H, m), 0.89 (3H, d, 6.5), 0.89 (3H, d, 6.5), 1.63–1.52 (2H, m), 1.28 (3H, d, 7), 1.30 (3H, d, 7), 1.06 (3H, t, 7.5), 13.22 (1H, s), 13.18 (1H, brs), 2.49 (1H, brs), 1.63 (1H, d, 11.5)
8. $^{13}$C NMR spectrum:
   Spectrum $^{13}$C-shift measured in D-chloroform 209.1 (s), 207.8 (s), 169.7 (s), 168.7 (s), 135.7 (d), 115.1 (s), 111.9 (s), 105.1 (d), 94.1 (d), 71.0 (d), 62.5 (d), 61.8 (s), 59.8 (d), 48.3 (d), 38.4 (t), 37.5 (t), 34.9 (d), 26.0 (d), 23.8 (q), 21.9 (q), 20.6 (t), 19.7 (q), 19.1 (q), 10.5 (q)
9. Solubility:
   soluble: ethyl acetate, chloroform and dimethyl sulfoxide
   insoluble: neutral water
10. High performance liquid chromatography:
    column: J'sphere ODS-H80, inside diameter: 4.6 mm, length: 75 mm (manufactured by YMC Co., Ltd.)
    solvent: acetonitrile/10 mM potassium dihydrogenphosphate buffer (pH 3.5)=6:4
    flow rate: 1 mL/min detection wavelength: ultraviolet absorption at 254 nm
    retention time: 4.8 min
11. Thin layer chromatography:
    carrier: silica gel 60 F254 (manufactured by Merck Germany)

developing solvent: toluene/methanol (9:1)
Rf value: 0.23

Analysis data of the structure of VD1207A2
1. Color and property: white powder
2. Molecular formula: $C_{24}H_{35}O_8$
3. Mass spectrum (FAB-MS): m/z 451 $(M+H)^+$
4. Specific rotation: $[\alpha]^D_{23}$–6.2 (c 0.1, $CHCl_3$)
5. Ultraviolet absorption spectrum:
   neutral methanol: $\lambda$max nm($\epsilon$): 258 (63900), 325 (9500)
   acidic methanol: $\lambda$max nm($\epsilon$): 257 (63900), 325 (9400)
   basic methanol: $\lambda$max nm($\epsilon$): 261 (25100), 317 (23400) 347 (25000)
6. Infrared absorption spectrum:
   Measured in a KBr powder. Main absorptions (wave number, $cm^{-1}$) 3440, 2960, 1640, 1590, 1490, 1470, 1350, 1210, 1160, 1090, 1040, 970, 930, 900, 830, 730, 690, 590, 540, 460
7. $^1H$ NMR spectrum:
   Spectrum $^1H$-shift (J value) measured in D-chloroform 8.46 (1H, s), 6.46 (1H, s), 5.01 (1H, d, 3), 4.34 (1H, ddd, 12, 7, 1.5), 4.21 (1H, ddd, 12, 11.5, 4.5), 3.31 (1H, t, 6.5), 3.69 (1H, ddd, 10.5, 7, 3.5), 1.91 (1H, ddd, 13.5, 10.5, 5), 1.66 (1H, m), 2.03 (1H, ddd, 12, 4.5, 1.5), 1.45 (1H, ddd, 12, 12, 12), 3.57 (1H, sept, 7), 1.50 (1H, m), 0.91 (3H, d, 6.5) 0.91 (3H, d, 6.5), 1.64 (2H, m), 1.29 (3H, d, 7), 1.30 (3H, d, 7), 1.10 (3H, t, 7.5), 13.21 (1H, s), 13.21 (1H, s), 2.59 (1H, d, 3), 1.54 (1H, d, 11.5)
8. $^{13}C$ NMR spectrum:
   Spectrum $^{13}C$-shift measured in D-chloroform 208.9 (s), 206.6 (s), 169.9 (s), 169.2 (s), 135.5 (d), 114.6 (s), 112.0 (s), 105.4 (d), 94.5 (d), 70.6 (d), 62.5 (d), 61.8 (s), 59.8 (d), 47.7 (d), 39.2 (t), 37.1 (t), 34.8 (d), 26.1 (d), 23.7 (q), 22.0 (q), 20.6 (t), 19.6 (q), 19.2 (q), 10.5 (q)
9. Solubility:
   soluble: ethyl acetate, chloroform and dimethyl sulfoxide
   insoluble: neutral water
10. High performance liquid chromatography:
    column: J'sphere ODS-H80, inside diameter: 4.6 mm, length:
    75 mm (manufactured by YMC Co., Ltd.)
    solvent: acetonitrile/10 mM potassium dihydrogenphosphate buffer (pH 3.5)=6:4
    flow rate: 1 mL/min
    detection: ultraviolet absorption at 254 nm
    retention time: 4.8 min
11. Thin layer chromatography:
    carrier: silica gel 60 F254 (manufactured by Merck Germany)
    developing solvent: toluene/methanol (9:1)
    Rf value: 0.17

Example 4

Purification and Analysis of the Structure of VD1207B

The fraction containing the B component obtained in Example 1 was dissolved in a small amount of ethyl acetate and subjected to a thin layer chromatograph plate (silica gel 60 No. 13895, manufactured by Merck Germany) using a developing solvent (toluene:acetone=7:3) to carry out preparative thin layer chromatography. After the development was completed, the spot of the B component was confirmed using a UV lamp (254 nm) and the B component was eluted with a mixed solvent of ethyl acetate/methanol (1:1), followed by evaporating to dryness.

The resulting residue was dissolved in a small amount of ethyl acetate and subjected to a thin layer chromatograph plate (silica gel 60 No. 5744, manufactured by Merck Germany) using a developing solvent (toluene:methanol=9:1) to carry out preparative thin layer chromatography. After the development was completed, the spot of the B component was confirmed using a UV lamp (254 nm), and the B component was eluted using a mixed solvent of ethyl acetate/methanol (1:1), followed by evaporating to dryness. The resulting residue was freeze dried to give a pure pale orange powder of VD1207B in amounts of 61 mg.

Analysis data of the structure of VD1207B
1. Color and property: pale orange powder
2. Molecular formula: $C_{25}H_{36}O_9$
3. Mass spectrum (FAB-MS): m/z 481 $(M+H)^+$
4. Specific rotation: $[\alpha]^D_{21}$–97.7 (c 0.1, $CHCl_3$)
5. Ultraviolet absorption spectrum:
   neutral methanol: $\lambda$max nm($\epsilon$): 254 (21300), 276 (16800) 341 (8500)
   acidic methanol: $\lambda$max nm($\epsilon$): 253 (27700), 276 (19100), 353 (7700)
   basic methanol: $\lambda$max nm($\epsilon$): 278 (18200), 332 (24600)
6. Infra red absorption spectrum:
   Measured in a KBr powder. Main absorptions (wave number, $cm^{-1}$) 3360, 2960, 1630, 1450, 1380, 1300, 1260, 1180, 1090, 1040, 930, 830, 750, 680, 590
7. $^1H$ NMR spectrum:
   Spectrum $^1H$-shift (J value) measured in D-chloroform 10.42 (1H, s), 8.08 (1H, s), 4.97 (H, d, 3), 4.33 (1H, d, 6), 4.40 (1H, ddd, 12, 7, 2), 4.19 (1H, ddd, 12, 12, 5), 3.28 (1H, t, 6.5), 3.23 (3H, s), 3.61 (1H, m), 2.05 (1H, ddd, 12, 5, 2) 1.44 (1H, ddd, 12, 12, 12), 1.92 (1H, sept, d, 7, 7), 1.80 (2H, m), 1.64 (2H, qd, 7.5, 6.5), 1.28 (2H, m), 0.93 (3H, d, 6.5), 0.93 (3H, d, 6.5), 0.89 (3H, d, 7.5), 1.08 (3H, t, 7.5), 14.17 (1H, brs), 12.97 (1H, brs), 2.89 (1H, s), 1.56 (1H, d, 12)
8. $^{13}C$ NMR spectrum:
   Spectrum $^{13}C$-shift measured in D-chloroform 207.2 (s), 194.4 (d), 167.9 (s), 167.3 (s), 137.6 (d), 120.3 (s), 113.0 (s), 109.2 (s), 94.5 (d), 80.6 (d), 69.6 (d), 62.6 (d), 61.8 (s), 59.7 (d), 57.2 (q), 49.8 (d), 37.1 (t), 33.8 (d), 33.9, 31.8 (t), 20.6 (t), 20.6 (t), 18.7 (q), 17.6 (q), 14.1 (q), 10.5 (q)
9. Solubility:
   soluble: ethyl acetate, chloroform and dimethyl sulfoxide
   insoluble: neutral water
10. High performance liquid chromatography:
    column: J'sphere ODS-H80, inside diameter: 4.6 mm, length: 75 mm (manufactured by YMC Co., Ltd.)
    solvent: acetonitrile/10 mM potassium dihydrogenphosphate buffer (pH 3.5)=6:4
    flow rate: 1 mL/min
    detection wavelength: ultraviolet absorption at 254 nm
    retention time: 5.4 min Example 5

Purification and Structure Analysis of VD1207C

The fraction containing the C component obtained in Example 1 was dissolved in a small amount of dimethyl sulfoxide and then subjected to fractionating HPLC (column: J'sphere ODS-H80, inside diameter: 20 mm, length: 250 mm, manufactured by YMC Co., Ltd., mobile phase: acetonitrile/10 mM potassium dihydrogenphosphate buffer (pH 3.5)=6:4, flow rate: 12 ml/min, detection: ultraviolet absorption at 254 nm, retention time: 31.3 min). This fractionating operation was repeated and the eluates showing single peak of the C component were mixed and extracted with ethyl acetate after acetonitrile was evaporated. The ethyl acetate layer was washed with deionized water and then evaporated to dryness.

The resulting residue was dissolved in ethyl acetate, a small amount of silica gel (Wakogel C-200, manufactured by Wako Pure Chemical Industries, Ltd.) was added thereto, and the solvent was evaporated. The resulting residue was subjected to a silica gel column (inside diameter: 20 mm, length: 500 mm) washed with a mixed solvent of hexane/acetone (95:5) and a similar mixed solvent (90:10), and eluted with a similar mixed solvent (80:20). The eluates containing the C component were mixed and the mixture was concentrated to dryness.

The resulting residue was dissolved in a small amount of ethyl acetate, a small amount of silica gel (Wakogel C-200, manufactured by Wako Pure Chemical Industries, Ltd.) was added thereto and the solvent was evaporated. The resulting residue was subjected to a silica gel column (inside diameter: 20 mm, length: 500 mm), washed with toluene and eluted with a mixed solvent of toluene/methanol=98:2. The eluates containing the C component were mixed and the mixture was concentrated to dryness.

The resulting residue was dissolved in a small amount of methanol, subjected to Sephadex LH-20 column (inside diameter: 20 mm, length: 950 mm, manufactured by Pharmacia Fine Chemicals AB) and eluted with methanol. The eluates containing the C component were mixed and the mixture was evaporated to dryness. The resulting residue was freeze-dried to give 256 mg of VD1207C as a pure white powder.

Analysis data of the structure of VD1207C

1. Color and property: white powder
2. Molecular formula:° $C_{25}H_{36}O_8$
3. Mass spectrum (FAB-MS): m/z 481 (M+H)$^+$
4. Specific rotation: $[\alpha]^D_{21}$+50.2 (c 0.1, CHCl$_3$)
5. Ultraviolet absorption spectrum:
   neutral methanol: λmax nm(ε): 253 (19500), 277 (16300) 341 (8700)
   acidic methanol: λmax nm(ε): 253 (25400), 277 (18400), 352 (7600)
   basic methanol: λmax nm(ε): 277 (17100), 334 (25200)
6. Infrared absorption spectrum:
   Measured in a KBr powder. Main absorptions (wave number, cm$^{-1}$) 2960, 1640, 1460, 1390, 1300, 1250, 1170, 1090, 1040, 930, 830, 750, 680, 590
7. $^1$H NMR spectrum:
   Spectrum $^1$H-shift (J value) measured in D-chloroform 10.43 (1H, s), 8.05 (1H, s), 4.96 (1H, d, 2.5), 4.34 (1H, d, 6.5), 4.41 (1H, ddd, 11.5, 7.5, 1.5), 4.19 (1H, ddd, 11.5, 11.5, 5), 3.27 (1H, t, 6.5), 3.22 (3H, s), 3.68 (1H, ddd, 9.5, 7.5, 4.5), 2.03 (1H, ddd, 11, 5, 1.5), 1.48 (1H, ddd, 11.5, 11.5, 11), 1.96 (1H, m) 1.82 (2H, m), 1.60 (2H, m), 1.24 (2H, m), 0.88 (3H, d, 6.5), 0.96 (3H, d, 6.5), 0.88 (3H, t, 7.5), 1.07 (3H, t, 7.5), 14.21 (1H, brs), 12.99 (1H, brs), 2.99 (1H, d, 2.5), 1.62 (1H, d, 11.5)
8. $^{13}$C NMR spectrum:
   Spectrum $^{13}$C-shift measured in D-chloroform 207.3 (s), 194.4 (d), 167.9 (s), 167.4 (s), 137.5 (d), 120.3 (s), 113.2 (s), 109.1 (s), 94.5 (d), 80.5 (d), 69.8 (d), 62.6 (d), 61.8 (s), 59.7 (d), 57.2 (q), 49.3 (d), 36.9 (t), 33.7 (d), 32.1 (t) 20.7 (t), 20.6 (t), 18.7 (q), 17.9 (q), 14.2 (q), 10.5 (q)
9. Solubility:
   soluble: ethyl acetate, chloroform and dimethyl sulfoxide
   insoluble: neutral water
10. High performance liquid chromatography:
    column: J'sphere ODS-H80, inside diameter: 4.6 mm, length: 75 mm (manufactured by YMC Co., Ltd.)
    solvent: acetonitrile/10 mM potassium dihydrogenphosphate buffer (pH 3.5)=6:4
    flow rate: 1 mL/min
    detection wavelength: ultraviolet absorption at 254 nm
    retention time: 6.0 min Example 6

Purification and Analysis of the Structure of VD1207D

The fraction containing the D component obtained in Example 1 was dissolved in a small amount of dimethyl sulfoxide and then subjected to fractionating HPLC (column: J'sphere ODS-H80, inside diameter: 20 mm, length: 250 mm, manufactured by YMC Co., Ltd., mobile phase: acetonitrile/10 mM potassium dihydrogenphosphate buffer (pH 3.5)=6:4, flow rate: 12 ml/min, detection: ultraviolet absorption at 254 nm, retention time: 37.1 min). This fractionating operation was repeated and the eluates showing single peak of the D component were mixed and extracted with ethyl acetate after acetonitrile was evaporated. The ethyl acetate layer was washed with deionized water and then evaporated to dryness.

The resulting residue was dissolved in a small amount of ethyl acetate and subjected to a thin layer chromatograph plate (silica gel 60 No. 13895, manufactured by Merck Germany) using a developing solvent (hexane:acetone=7:3) to carry out preparative thin layer chromatography. After the development was completed, the spot of the D component was confirmed using a UV lamp (254 nm) and the D component was eluted with a mixed solvent of ethyl acetate/methanol (1:1), followed by evaporating to dryness.

The resulting residue was dissolved in a small amount of ethyl acetate and subjected to a thin layer chromatograph plate (silica gel 60 No. 5744, manufactured by Merck Germany) using a developing solvent (toluene:methanol=9:1) to carry out preparative thin layer chromatography. After the development was completed, the spot of the D component was confirmed using a UV lamp (254 nm), and the D component was eluted using a mixed solvent of ethyl acetate/methanol (1:1), followed by evaporating to dryness. The resulting residue was freeze-dried to give a pure pale orange powder of VD1207D in amounts of 64 mg.

Analysis data of the structure of VD1207D

1. Color and property: pale orange powder
2. Molecular formula: $C_{24}H_{34}O_8$
3. Mass spectrum (FAB-MS): m/z 451 (M+H)$^+$
4. Specific rotation: $[\alpha]^D_{21}$−13.0 (c 0.1, CHCl$_3$)
5. Ultraviolet absorption spectrum:
   neutral methanol: λmax nm(ε): 255 (23000), 276 (16300), 352 (7800)

acidic methanol: λmax nm(ε): 255 (27300), 276 (18000), 357 (7800)

basic methanol: λmax nm(ε): 279 (18000), 338 (26400)

6. Infrared absorption spectrum:

Measured in a KBr powder. Main absorptions (wave number, cm$^{-1}$) 3440, 2960, 2870, 1630, 1460, 1390, 1300, 1270, 1190, 1090, 1040, 930, 830, 680, 620, 550

7. $^1$H NMR spectrum:

Spectrum $^1$H-shift (J value) measured in D-chloroform 10.41 (1H, s), 7.74 (1H, s), 4.99 (1H, d, 3), 4.38 (1H, ddd, 11.5, 9, 1.5), 4.20 (1H, ddd, 11.5, 11.5, 4.5), 3.29 (1H, dd, 7, 6), 3.56 (1H, ddd, 9, 9, 4), 2.47 (1H, dd, 13.5, 7), 2.42 (1H, dd, 13.5, 7), 2.02 (1H, ddd, 12, 4.5, 1.5), 1.42 (1H, ddd, 12, 11.5, 11.5), 1.83 (2H, m), 1.91 (1H, m), 0.92 (3H, d, 6.5), 0.92 (3H, d, 6.5), 1.61 (2H, m), 1.25 (2H, m), 0.88 (3H, t, 7.5), 1.08 (3H, t, 7.5), 14.15 (1H, brs), 12.98 (1H, brs), 2.74 (1H, d, 3), 1.55 (1H, d, 11.5)

8. $^{13}$C NMR spectrum:

Spectrum $^{13}$C-shift measured in D-chloroform 206.7 (s), 194.3 (d), 168.0 (s), 167.5 (s), 139.4 (d), 121.0 (s), 112.5 (s), 109.3 (s), 94.5 (d), 69.8 (d), 62.4 (d), 61.8 (s), 59.8 (d), 49.4 (d), 37.9 (t), 37.3 (t), 32.1 (t), 28.3 (d), 22.3 (q) 22.2 (q), 20.6 (t), 20.6 (t), 14.2 (q), 10.5 (q)

9. Solubility:

soluble: ethyl acetate, chloroform and dimethyl sulfoxide insoluble: neutral water 10. High performance liquid chromatography:

column: J'sphere ODS-H80, inside diameter: 4.6 mm, length: 75 mm (manufactured by YMC Co., Ltd.)

solvent: acetonitrile/10 mM potassium dihydrogenphosphate buffer (pH 3.5)=6:4 flow rate: 1 mL/min detection wavelength: ultraviolet absorption at 254 nm retention time: 7.0 min

Example 7

Purification and Analysis of the Structure of VD1207E

The fraction containing the E component obtained in Example 1 was dissolved in a small amount of dimethyl sulfoxide and then subjected to fractionating HPLC (column: J'sphere ODS-H80, inside diameter: 20 mm, length: 250 mm, manufactured by YMC Co., Ltd., mobile phase: acetonitrile/10 mM potassium dihydrogenphosphate buffer (pH 3.5)=6:4, flow rate: 12 ml/min, detection: ultraviolet absorption at 254 nm, retention time: 37.8 min). This fractionating operation was repeated and the eluates showing single peak of the E component were mixed and extracted with ethyl acetate after acetonitrile was evaporated. The ethyl acetate layer was washed with deionized water and then evaporated to dryness.

The resulting residue was dissolved in a small amount of ethyl acetate and subjected to a thin layer chromatograph plate (silica gel 60 No. 5744, manufactured by Merck Germany) using a developing solvent (toluene:methanol= 9:1) to carry out preparative thin layer chromatography. After the development was completed, the spot of the E component was confirmed using a UV lamp (254 nm) and the E component was eluted with a mixed solvent of ethyl acetate/methanol (1:1), followed by evaporating to dryness. The resulting residue was freeze-dried to give 16 mg of VD1207E as a pure white powder.

Analysis data of the structure of VD1207E

1. Color and property: white powder
2. Molecular formula: $C_{26}H_{38}O_9$
3. Mass spectrum (FAB-MS): m/z 495 (M+H)$^+$
4. Specific rotation: $[\alpha]^D_{21}$ –82.6 (c 0.1, CHCl$_3$)
5. Ultraviolet absorption spectrum:

neutral methanol: λmax nm(ε): 254 (22500), 276 (17700), 341 (9300)

acidic methanol: λmax nm(ε): 253 (29100), 276 (20100), 352 (8200)

basic methanol: λmax nm(ε): 277 (19400), 333 (26200)

6. Infrared absorption spectrum:

Measured in a KBr powder. Main absorptions (wave number, cm$^{-1}$) 3440, 2960, 1640, 1460, 1390, 1300, 1260, 1180, 1090, 1020, 930, 830, 740, 680, 590, 570

7. $^1$H NMR spectrum:

Spectrum $^1$H-shift (J value) measured in D-chloroform 10.42 (1H, s), 8.13 (1H, s), 4.95 (1H, d, 3), 4.35 (1H, d, 5.5), 4.33 (1H, ddd, 12, 7, 1.5), 4.17 (1H, ddd, 11.5, 11.5, 4.5), 3.28 (1H, dd, 7, 6), 3.23 (3H, s), 3.72 (1H, ddd, 10, 7, 3.5), 1.89 (1H, ddd, 13.5, 10, 4.5), 1.58 (1H, m), 2.02 (1H, ddd, 12, 4.5, 1.5), 1.47 (1H, ddd, 12, 12, 11.5), 1.92 (1H, sept, d, 7, 5.5), 1.46 (1H, m), 0.88 (3H, d, 6.5), 0.87 (3H, d, 6.5), 1.61 (2H, m), 0.91 (3H, d, 7), 0.92 (3H, d, 7), 1.08 (3H, t, 7.5), 14.21 (1H, s), 12.98 (1H, s), 2.69 (1H, brs), 1.53 (1H, d, 11.5)

8. $^{13}$C NMR spectrum:

Spectrum $^{13}$C-shift measured in D-chloroform 207.2 (s), 194.4 (d), 167.9 (s), 167.3 (s), 137.6 (d), 120.3 (s), 113.1 (s), 109.2 (s), 94.5 (d), 80.6 (d), 70.3 (d), 62.6 (d), 61.7 (s), 59.7 (d), 57.2 (q), 47.6 (d), 38.7 (t), 36.9 (t), 33.8 (d), 26.1 (d), 23.6 (q), 21.8 (q), 20.6 (t), 18.7 (q), 17.5 (q), 10.5 (q)

9. Solubility:

soluble: ethyl acetate, chloroform and dimethyl sulfoxide insoluble: neutral water 10. High performance liquid chromatography:

column: J'sphere ODS-H80, inside diameter: 4.6 mm, length: 75 mm (manufactured by YMC Co., Ltd.)

solvent: acetonitrile/10 mM potassium dihydrogenphosphate buffer (pH 3.5)=6:4 flow rate: 1 mL/min detection wavelength: ultraviolet absorption at 254 nm retention time: 7.4 min

Example 8

Purification and Structure Analysis of VD1207F

The fraction containing the F component obtained in Example 1 was dissolved in a small amount of dimethyl sulfoxide and subjected to a column (inside diameter: 30 mm, length: 450 mm) of YMC-GEL ODS-AM 120-S50 (manufactured by YMC Co., Ltd.) which was pre-equilibrated with a mixed solution of acetonitrile/10 mM potassium dihydrogenphosphate buffer (pH: 3.5)=(45:55). The treated product was washed with a mixed solvent having the same composition as the aforementioned and also with a mixed solvent having the same components as the aforementioned mixture solvent but differed in the ratio of each component was (1:1). In succession, similar mixed solvents (the ratios of the components of each mixture solvent: 55:45 and 60:40) were used in order of descending polarity to elute. The eluates containing the F component were collected and extracted with ethyl acetate after acetonitrile was evaporated. The ethyl acetate layer was washed with deionized water and evaporated to dryness.

The resulting residue was dissolved in ethyl acetate, to which was then added a small amount of silica gel (Silica Gel FL100D, manufactured by Fuji Silysia Chemical Ltd.) and the solvent was evaporated. The resulting residue was subjected to a silica gel column (inside diameter: 20 mm, length: 500 mm), washed with a mixed solvent of hexane and hexane/acetone (95:5), and eluted with similar mixed solvents (90:10) and (85:15). The eluates containing the F component were mixed and the mixture was concentrated to dryness.

The resulting residue was dissolved in ethyl acetate, to which was then added a small amount of silica gel (Silica Gel FL100D, manufactured by Fuji Silysia Chemical Ltd.) and the solvent was evaporated. The resulting residue was subjected to a silica gel column (inside diameter: 20 mm, length: 500 mm), washed with toluene and eluted with a mixed solvent of toluene/methanol=99:1 and a similar mixed solvents (98:2). The eluates containing the F component were mixed and the mixture was concentrated to dryness.

The resulting residue was dissolved in a small amount of ethyl acetate and subjected to a thin layer chromatograph plate (silica gel 60 No. 5744, manufactured by Merck Germany) using a developing solvent (toluene:methanol= 9:1) to carry out preparative thin layer chromatography. After the development was completed, the spot of the F component was confirmed using a UV lamp (254 nm), and the F component was eluted with a mixed solvent of ethyl acetate/methanol (1:1), followed by evaporating to dryness. The resulting residue was freeze-dried to give a pure pale orange powder of VD1207F in amounts of 125 mg.

Analysis data of the structure of VD1207F

1. Color and property: pale orange powder
2. Molecular formula: $C_{26}H_{38}O_9$
3. Mass spectrum (FAB-MS): m/z 495 (M+H)$^+$
4. Specific rotation: $[\alpha]^D_{21}$+54.1 (c 0.1, CHCl$_3$)
5. Ultraviolet absorption spectrum:
   neutral methanol: λmax nm(ε): 254 (14900), 278 (12100), 348 (5700)
   acidic methanol: λmax nm(ε): 254 (17400), 278 (13300), 351 (5600)
   basic methanol: λmax nm(ε): 277 (12400), 338 (20000)
6. Infrared absorption spectrum:
   Measured in a KBr powder. Main absorptions (wave number, cm$^{-1}$) 3420, 2960, 1630, 1460, 1380, 1300, 1260, 1180, 1090, 1040, 930, 830, 740, 680, 590, 570
7. $^1$H NMR spectrum:
   Spectrum $^1$H-shift (J value) measured in D-chloroform 10.42 (1H, s), 8.08 (1H, s)., 4.94 (1H, d, 2.5), 4.34 (1H, d, 6), 4.30 (1H, m), 4.17 (1H, ddd, 12, 12, 4.5), 3.27 (1H, dd, 7, 6), 3.22 (3H, s), 3.75 (1H, ddd, 10.5, 7, 3.5), 1.90 (1H, ddd, 13, 10.5, 4.5), 1.59 (1H, m), 2.02 (1H, ddd, 12.5, 5, 2), 1.46 (1H, ddd, 12, 12, 12), 1.90 (1H, sept, d, 7, 7), 1.46 (2H, m), 0.88 (3H, d, 6.5), 0.86 (3H, d, 6.5), 1.59 (2H, m), 0.90 (3H, d, 7), 0.94 (3H, d, 7), 1.07 (3H, t, 7.5), 14.21 (1H, brs), 12.98 (1H, brs), 2.95 (1H, d, 3), 1.59 (1H, d, 12)
8. $^{13}$C NMR spectrum:
   Spectrum $^{13}$C-shift measured in D-chloroform 207.2 (s), 194.4 (d), 167.9 (s), 167.3 (s), 137.6 (d), 120.2 (s), 113.3 (s), 109.2 (s), 94.5 (d), 80.7 (d), 70.5 (d), 62.7 (d), 61.7 (s), 59.7 (d), 57.2 (q), 47.2 (d), 38.7 (t), 36.6 (t), 33.9 (d), 26.2 (t), 23.6 (q), 21.9 (q), 20.6 (t), 18.7 (q), 17.7 (q), 10.5 (q),
9. Solubility:
   soluble: ethyl acetate, chloroform, dimethylsulfoxide
   insoluble: neutral water
10. High performance liquid chromatography:
    column: J'sphere ODS-H80, inside diameter: 4.6 mm, length: 75 mm (manufactured by YMC Co., Ltd.)
    solvent: acetonitrile/10 mM potassium dihydrogenphosphate buffer (pH 3.5)=6:4
    flow rate: 1 mL/min
    detection wavelength: ultraviolet absorption at 254 nm
    retention time: 8.0 min Example 9

Purification and Structure Analysis of VD1207F'

In the fraction containing the F' component obtained in Example 1 was dissolved and then subjected to fractionating HPLC (column: J'sphere ODS-H80, inside diameter: 20 mm, length: 250 mm, manufactured by YMC Co., Ltd., mobile phase: acetonitrile/10 mM potassium dihydrogenphosphate buffer (pH 3.5)=60:40, flow rate: 12 ml/min, detection: ultraviolet absorption at 254 nm, retention time: 48.3 min). This fractionating operation was repeated and the eluates showing the peak of the F' component were mixed and extracted with ethyl acetate after acetonitrile was evaporated. The ethyl acetate layer was washed with deionized water and then evaporated to dryness. The resulting residue was freeze-dried to give 2.8 mg of VD1207F' as a pure pale yellow powder.

Analysis data of the structure of VD1207F'

1. Color and property: pale yellow powder
2. Molecular formula: $C_{26}H_{39}O_9$
3. Mass spectrum (FAB-MS): m/z 495 (M+H)$^+$
4. Specific rotation: $[\alpha]^D_{21}$+4.4 (c 0.1, CHCl$_3$)
5. Ultraviolet absorption spectrum:
   neutral methanol: λmax nm(ε): 253 (21200), 286 (24500), 340 (11600)
   acidic methanol: λmax nm(ε): 253 (24100), 285 (25100), 346 (10000)
   basic methanol: λmax nm(ε): 276 (16500), 346 (40300)
6. Infrared absorption spectrum:
   Measured in a KBr powder. Main absorptions (wavenumber, cm$^{-1}$) 3330, 2960, 2870, 1720, 1620, 1460, 1380, 1300, 1170, 1090, 930, 830, 680, 590
7. $^1$H NMR spectrum:
   Spectrum $^1$H-shift (J value) measured in D-chloroform 10.43 (1H, s), 8.03 (1H, s), 4.98 (1H, d, 2.5), 4.34 (1H, d, 6), 4.40 (1H, ddd, 11.5, 8, 1.5), 4.19 (1H, ddd, 11.5, 11.5, 5), 3.28 (1H, dd, 7, 6), 3.23 (3H, s), 3.61 (1H, td, 8.5, 5), 2.04 (1H, m), 1.43 (1H, ddd, 11.5, 11.5, 11.5), 1.92 (1H, m), 1.84 (2H, m) or 1.19 (2H, m), 1.84 (2H, m) or 1.19 (2H, m), 1.28 (2H, m), 1.60 (2H, m) 0.90 (3H, d), 0.94 (3H, d, 7), 0.84 (3H, t, 7), 1.08 (3H, t, 7.5), 14.20 (1H, brs), 12.99 (1H, brs), 2.66 (1H, d, 3.5), 1.53 (1H, s)
8. $^{13}$C NMR spectrum:
   Spectrum $^{13}$C-shift measured in D-chloroform 207.2 (s), 194.3 (d), 167.8 (s), 167.3 (s), 137.4 (d), 120.3 (s), 113.1 (s), 109.1 (s), 94.5 (d), 80.5 (d), 69.7 (d), 62.5 (d), 61.7 (s), 59.7 (d), 57.2 (d), 49.5 (d), 36.9 (t), 33.8 (t), 29.6 (t), 29.5 (t), 22.8 (t), 20.6 (t), 18.6 (q), 17.6 (q), 13.8 (q), 10.5 (q)

9. Solubility:
   soluble: ethyl acetate, chloroform and dimethyl sulfoxide
   insoluble: neutral water
10. High performance liquid chromatography:
    column: J'sphere ODS-H80, inside diameter: 4.6 mm, length: 75 mm (manufactured by YMC Co., Ltd.)
    solvent: acetonitrile/10 mM potassium dihydrogenphosphate buffer (pH 3.5)=6:4
    flow rate: 1 mL/min
    detection wavelength: ultraviolet absorption at 254 nm
    retention time: 8.2 min Example 10

Purification and Structure Analysis of VD1207G', G1 and G2

The fraction containing the G1 and G2 components obtained in Example 1 was dissolved in a small amount of dimethyl sulfoxide and then subjected to fractionating HPLC (column: J'sphere ODS-H80, inside diameter: 20 mm, length: 250 mm, manufactured by YMC Co., Ltd., mobile phase: acetonitrile/10 mM potassium dihydrogenphosphate buffer (pH 3.5)=65:35, flow rate: 12 ml/min, detection: ultraviolet absorption at 254 nm, retention time; G1 and G2: 33.8 min, G': 35.5 min). This fractionating operation was repeated and the eluates showing each peak of the G1 and G2 components and the eluates showing the peak of the G' component were mixed respectively and extracted with ethyl acetate after acetonitrile was evaporated. The ethyl acetate layer was washed with deionized water and then evaporated to dryness to give the fraction containing the G1 and G2 components and 4mg of VD1207G' as a pure pale yellow powder.

The fraction containing the G1 and G2 components was dissolved in a small amount of ethyl acetate and subjected to a thin layer chromatograph plate (silica gel 60 No. 5744, manufactured by Merck Germany) using a developing solvent (hexane:acetone=7:3) to carry out preparative thin layer chromatography. After the development was completed, each spot of the G1 and G2 components was confirmed using a UV lamp (254 nm) and each component was mixed and eluted with a mixed solvent of ethyl acetate/methanol (1:1), followed by evaporating to dryness.

The resulting residue was dissolved in a small amount of ethyl acetate and subjected to a thin layer chromatograph plate (silica gel 60 No. 5744, manufactured by Merck Germany) using a developing solvent (toluene:methanol= 17:3) to carry out preparative thin layer chromatography. After the development was completed, each spot of the G1 and G2 components was confirmed using a UV lamp (254 nm) (Rf value; G1: 0.30, G2: 0.24) and each of the G1 and G2 components was eluted with a mixed solvent of ethyl acetate/methanol (1:1), followed by evaporating to dryness. The resulting residue was freeze-dried to give each pure white powder of VD1207 G1 and G2 in amounts of 7 mg and 8 mg, respectively. Analysis data of the structure of VD1207G'

1. Color and property: pale yellow powder
2. Molecular formula: $C_{25}H_{37}O_8$
3. Mass spectrum (FAB-MS): m/z 465 (M+H)$^+$
4. Specific rotation: $[\alpha]^P_{23}$+2.3 (c 0.04, CHCl$_3$)
5. Ultraviolet absorption spectrum:
   neutral methanol: λmax nm(ε): 254 (86600), 277 (59500), 355 (26800)
   acidic methanol: λmax nm(ε): 255 (91500), 277 (61500) 356 (26100)
   basic methanol: λmax nm(ε): 279 (62800), 337 (84800)
6. Infrared absorption spectrum:
   Measured in a KBr powder. Main absorptions (wave number, cm$^{-1}$) 3390, 2960, 2870, 1630, 1460, 1390, 1300, 1180, 1090, 1040, 930, 830, 680, 620, 550
7. $^1$H NMR spectrum:
   Spectrum $^1$H-shift (J value) measured in D-chloroform 10.42 (1H, s), 7.73 (1H, s), 5.00 (1H, d, 2.5), 4.38 (1H, ddd, 11.5, 8, 1.5), 4.20 (1H, ddd, 11.5, 11.5, 5), 3.30 (1H, dd, 7, 6), 3.54 (1H, td, 8, 5.5), 2.48 (1H, dd, 13.5, 7), 2.42 (1H, dd, 13.5, 7), 2.03 (1H, ddd, 12.5, 5, 1.5), 1.42 (1H, ddd, 12, 12, 12), 1.84 (2H, m), 1.20 (2H, m), 1.91 (1H, m), 1.28 (2H, m), 0.93 (3H, d, 6.5), 0.92 (3H, d, 6.5), 1.63 (2H, m), 0.85 (3H, t, 7), 1.09 (3H, t, 7.5), 14.16 (1H, s), 12.99 (1H, s), 2.69 (1H, d, 3), 1.50 (1H, d, 11.5)
8. $^{13}$C NMR spectrum:
   Spectrum $^{13}$C-shift measured in D-chloroform 206.7 (s), 194.3 (d), 168.0 (s), 167.5 (s), 139.5 (d), 121.0 (s), 112.6 (s), 109.4 (s), 94.5 (d), 69.8 (d), 62.4 (d), 61.8 (s), 59.8 (d), 49.6 (d), 37.9 (t) 37.3 (t), 29.7 (t), 29.5 (t), 28.3 (d) 22.8 (t), 22.4 (q), 22.2 (q), 20.6 (t), 13.8 (q), 10.5 (q)
9. Solubility:
   soluble: ethyl acetate, chloroform and dimethyl sulfoxide
   insoluble: neutral water
10. High performance liquid chromatography:
    column: J'sphere ODS-H80, inside diameter: 4.6 mm, length: 75 mm, (manufactured by YMC Co., Ltd.)
    solvent: acetonitrile/10 mM potassium dihydrogenphosphate buffer (pH 3.5)=6:4
    flow rate : 1 mL/min
    detection wavelength: ultraviolet absorption at 254 nm
    retention time: 9.8 min Analysis data of the structure of VD1207G1
1. Color and property: white powder
2. Molecular formula: $C_{25}H_{36}O_8$
3. Mass spectrum (FAB-MS): m/z 465 (M+H)$^+$
4. Specific rotation: $[\alpha]^P_{21}$–11.5 (c 0.1, CHCl$_3$)
5. Ultraviolet absorption spectrum:
   neutral methanol: λmax nm(ε): 254 (25600), 276 (17200), 355 (7800)
   acidic methanol: λmax nm(ε): 255 (29800), 276 (19500), 356 (8400) basic methanol: λmax nm(ε): 279 (20000), 337 (27200)
6. Infrared absorption spectrum:
   Measured in a KBr powder. Main absorptions (wave number, cm$^{-1}$) 3440, 2960, 2870, 1630, 1460, 1390, 1300, 1190, 1100, 1030, 930, 910, 820, 680, 620, 550
7. $^1$H NMR spectrum:
   Spectrum $^1$H-shift (J value) measured in D-chloroform 10.42 (1H, s), 7.74 (1H, s), 5.01 (1H, d, 3.5), 4.38 (1H, ddd, 12, 8.5, 2), 4.20 (1H, ddd, 12, 11.5, 4.5), 3.34 (1H, dd, 7, 6), 3.56 (1H, ddd, 9, 8.5, 4.5), 2.03 (1H, ddd, 12, 4.5, 2), 1.42 (1H, ddd, 12, 12, 12), 2.47 (1H, dd, 13.5, 7), 2.42 (1H, dd, 13.5, 7), 1.83 (2H, m), 1.66 (1H, m), 1.55 (1H, m), 1.91 (1H, m), 1.55 (2H, m), 1.24 (2H, m), 0.93 (3H, d, 6.5), 0.92 (3H, d, 6.5), 0.99 (3H, d, 7.5), 0.89 (3H, t, 7.5), 14.15 (1H, s), 12.99 (1H, s), 2.52 (1H, d, 3.5), 1.50 (1H, d, 11.5)
8. $^{13}$C NMR spectrum:
   Spectrum $^{13}$C-shift measured in D-chloroform 206.7 (s), 194.3 (d), 168.0 (s), 167.5 (s), 139.4 (d), 121.0

(s), 112.5 (s), 109.4 (s), 94.5 (d), 69.8 (d), 62.4 (d), 61.5 (s), 58.6 (d), 49.4 (d), 37.9 (t), 37.3 (t), 32.1 (t), 31.2 (t), 29.3 (d), 28.3 (t), 22.3 (t), 20.6 (q), 19.9 (q), 14.2 (q), 13.9 (q),

9. Solubility:
   soluble: ethyl acetate, chloroform and dimethyl sulfoxide
   insoluble: neutral water
10. High performance liquid chromatography:
    column: J'sphere ODS-H80, inside diameter: 4.6 mm, length: 75 mm, (manufactured by YMC Co., Ltd.)
    solvent: acetonitrile/10 mM potassium dihydrogenphosphate buffer (pH 3.5)=6:4
    flow rate: 1 mL/min
    detection wavelength: ultraviolet absorption at 254 nm
    retention time: 9.4 min
11. Thin layer chromatography:
    carrier: silica gel 60 F254 (manufactured by Merck Germany)
    developing solvent: toluene/methanol (17:3)
    Rf value: 0.30

Analysis data of the structure of VD1207G2

1. Color and property: white powder
2. Molecular formula: $C_{25}H_{36}O_8$
3. Mass spectrum (FAB-MS): m/z 465 $(M+H)^+$
4. Specific rotation: $[\alpha]^D_{21}$ –11.2 (c 0.1, $CHCl_3$)
5. Ultraviolet absorption spectrum:
   neutral methanol: $\lambda$max nm($\epsilon$): 255 (28000), 277 (19200), 356 (8800)
   acidic methanol: $\lambda$max nm($\epsilon$): 255 (30900), 277 (20400) 356 (8700)
   basic methanol: $\lambda$max nm($\epsilon$): 278 (21100), 337 (28100)
6. Infrared absorption spectrum:
   Measured in a KBr powder. Main absorptions (wave number, $cm^{-1}$) 3440, 2960, 1640, 1460, 1390, 1340, 1300, 1270, 1190, 1090, 1040, 910, 880, 830, 730, 680, 620, 550
7. $^1$H NMR spectrum:
   Spectrum $^1$H-shift (J value) measured in D-chloroform 10.42 (1H, s), 7.78 (1H, s), 4.99 (1H, d, 3), 4.30 (1H, ddd, 11, 7.5, 1.5), 4.18 (1H, ddd, 12, 12, 4.5), 3.29 (1H, dd, 7, 6), 3.65 (1H, ddd, 10.5, 7, 3.5), 1.90 (1H, ddd, 13.5, 10.5, 4.5), 1.63 (1H, m), 2.50 (1H, dd, 14, 7), 2.41 (1H, dd, 14, 7), 1.99 (1H, ddd, 12.5, 5, 2), 1.45 (1H, ddd, 12.5, 12, 11), 1.92 (1H, sept, d, 7, 7), 1.45 (1H, m), 0.88 (3H, d, 6.5), 0.93 (3H, d, 6.5), 0.92 (3H, d, 6.5), 0.87 (3H, d, 6.5), 1.60 (3H, qd, 7, 7), 1.09 (3H, d, 7.5), 14.20 (1H, s) 13.00 (1H, s), 2.50 (1H, d, 3.5), 1.50 (1H, d, 12)
8. $^{13}$C NMR spectrum:
   Spectrum $^{13}$C-shift measured in D-chloroform 206.7 (s), 194.3 (d), 168.0 (s), 167.5 (s), 139.4 (d), 121.0 (s), 112.7 (s), 109.4 (s), 94.5 (d), 70.6 (d), 62.5 (d), 61.8 (s), 59.8 (d), 47.4 (d), 39.0 (t), 38.0 (t), 37.1 (t), 28.2 (d), 26.2 (d) 23.7 (q), 22.4 (q), 22.2 (q), 22.0 (q), 20.6 (t), 10.5 (q)
9. Solubility:
   soluble: ethyl acetate, chloroform and dimethyl sulfoxide
   insoluble: neutral water
10. High performance liquid chromatography:
    column: J'sphere ODS-H80, inside diameter: 4.6 mm, length: 75 mm (manufactured by YMC Co., Ltd.)
    solvent: acetonitrile/10 mM potassium dihydrogenphosphate buffer (pH3.5)=6:4
    flow rate: 1 mL/min
    detection wavelength: ultraviolet absorption at 254 nm
    retention time: 9.4 min
11. Thin layer chromatography:
    carrier: silica gel 60 F254 (manufactured by Merck Germany)
    developing solvent: toluene/methanol (17:3)
    Rf value: 0.24

Example 11

Purification and Structure Analysis of VD1207H

The fraction containing the H component obtained in Example 1 was dissolved in a small amount of dimethyl sulfoxide and then subjected to fractionating HPLC (column: J'sphere ODS-H80, inside diameter: 20 mm, length: 250 mm, manufactured by YMC Co., Ltd., mobile phase: acetonitrile/10 mM potassium dihydrogenphosphate buffer (pH 3.5)=65:35, flow rate: 12 ml/min, detection: ultraviolet absorption at 254 nm, retention time: 36.6 min). This fractionating operation was repeated and the eluates showing the single peak of the H component were mixed and extracted with ethyl acetate after acetonitrile was evaporated. The ethyl acetate layer was washed with deionized water and then evaporated to dryness. The resulting residue was dissolved in ethyl acetate, to which was then added a small amount of silica gel (Silica Gel FL100D, manufactured by Fuji Silysia Chemical Ltd.) and the solvent was evaporated. The resulting residue was subjected to a silica gel column (inside diameter: 20 mm, length: 380 mm), washed with a mixed solvent of hexane/acetone (95:5) and eluted with a similar mixed solvent (90:10). The eluates containing the H component were mixed and the mixture was concentrated to dryness.

The resulting residue was dissolved in a small amount of methanol, subjected to Sephadex LH-20 column (inside diameter: 20 mm, length: 950 mm, manufactured by Pharmacia Fine Chemicals AB) and eluted with methanol. The eluates containing the H component were mixed and the mixture was evaporated to dryness. The resulting residue was freeze-dried to give 75 mg of VD1207H as a pure white powder.

Analysis data of the structure of VD1207H

1. Color and property: pale yellow powder
2. Molecular: $C_{25}H_{36}O_8$
3. Mass spectrum (FAB-MS): m/z 465 $(M+H)^+$
4. Specific rotation: $[\alpha]^D_{21}$ –1.6 (c 0.1, $CHCl_3$)
5. Ultraviolet absorption spectrum:
   neutral methanol: $\lambda$max nm($\epsilon$): 255 (28000), 277 (19200), 356 (8800)
   acidic methanol: $\lambda$max nm($\epsilon$): 255 (30900), 277 (20400), 356 (8700)
   basic methanol: $\lambda$max nm($\epsilon$): 278 (21100), 337 (28100)
6. Infrared absorption spectrum:
   Measured in a KBr powder. Main absorptions (wave number, $cm^{-1}$) 3420, 2960, 2870, 2670, 1620, 1400, 1300, 1150, 1090, 1040, 910, 830, 760, 690, 620, 560
7. $^1$H NMR spectrum:
   Spectrum $^1$H-shift (J value) measured in D-chloroform 7.71 (1H, s), 5.01 (1H, d, 2.5), 4.38 (1H, ddd, 12, 8, 1.5), 4.20 (1H, ddd, 12, 11.5, 4.5), 3.30 (1H, dd, 7, 6), 3.58 (1H, ddd, 8.5, 8, 4.5), 2.47 (1H, dd, 13.5, 7), 2.41 (1H, dd, 13.5, 7), 2.02 (1H, ddd, 12, 4.5, 1.5), 1.42 (1H, ddd, 12, 12, 12), 2.79 (3H, s), 1.83 (2H, m), 1.92 (1H, m), 0.91 (3H, d, 6.5), 0.92 (3H, d, 6.5), 1.64 (2H, m), 1.25 (2H, m), 0.88 (3H, t, 7.5), 1.09 (3H, t, 8), 15.11 (1H, s), 14.73 (1H, s), 2.73 (1H, d, 2.5), 1.54 (1H, d, 11.5)

8. $^{13}C$ NMR spectrum:

Spectrum $^{13}C$-shift measured in D-chloroform 206.6 (s), 205.9 (s), 170.0 (s), 167.7 (s), 137.8 (d), 121.5 (s), 112.1 (s), 109.5 (s), 94.5 (d), 69.9 (d), 62.5 (d), 61.8 (s), 59.8 (d), 49.3 (d), 38.6 (t) 37.4 (t), 33.6 (q), 32.2 (t), 28.1 (d) 22.4 (q), 22.3 (q), 20.6 (t), 20.5 (t), 14.2 (q), 10.5 (q)

9. Solubility:

soluble: ethyl acetate, chloroform and dimethyl sulfoxide insoluble: neutral water 10. High performance liquid chromatography:

column: J'sphere ODS-H80, inside diameter: 4.6 mm, length: 75 mm, (manufactured by YMC Co., Ltd.)

solvent: acetonitrile/10 mM potassium dihydrogenphosphate buffer (pH 3.5)=6:4 flow rate: 1 mL/min detection wavelength: ultraviolet absorption at 254 nm retention time: 10.3 min

From the above analysis data, the structures of each compounds are shown in Table 1.

TABLE 1

| Compound | MW | $R^1$ | $R^2, R^3$ | $R^4$ | $R^5$ |
|---|---|---|---|---|---|
| A1 | 450 | H | =O | i—Pr | H |
| A2 | 450 | H | =O | i—Pr | H |
| B | 480 | CHO | $OCH_3$, H | Et | H |
| C | 480 | CHO | $OCH_3$, H | Et | H |
| D | 450 | CHO | H, H | Et | H |
| E | 494 | CHO | $OCH_3$, H | i—Pr | H |
| F | 494 | CHO | $OCH_3$, H | i—Pr | H |
| F' | 480 | CHO | $OCH_3$, H | n—Pr | H |
| G1 | 464 | CHO | H, H | Et | $CH_3$ |
| G2 | 464 | CHO | H, H | i—Pr | H |
| G' | 480 | CHO | H, H | n—Pr | H |
| H | 464 | $COCH_3$ | H, H | Et | H |
| U1 | 480 | H | =O | Et | H |
| U2 | 480 | H | =O | Et | H |

It is to be noted that B and C, E and F, A1 and A2, and U1 and U2 are epimers differing in the configuration at the "*" position, respectively.

Example 12

Antiangiogenic Effect

The antiangiogenic potency was evaluated by the inhibition of capillary formation in rat aorta model in which aorta pieces of rat were cultured in collagen gel. That is, the aorta excised from male rat of Sprague-Dawley strain (8–12 weeks age) was washed with a Hanks' solution so that fat tissues around there were removed minutely. The aorta was incised to prepare pieces of 2 mm square and they were allowed to stand in a 24-well plate holding the endothelial cells upside. Then, 500 µl of neutralized Type I collagen (Cell Matrix Type I-A; manufactured by Nitta Gelatin) were poured over each well and allowed to stand at room temperature for about 20 minutes in a clean bench to solidify the gel. After gelling, 500 µl of MCDB 131 medium (manufactured by Chlorella Kogyo) were added thereto followed by incubating in a $Co_2$ incubator (5% $CO_2$) at 37° C. On the next day, the culture medium was exchanged with 500 µl of MCDB 131 medium containing the sample and the incubation was continued. And, at the stage of the 7th day from the addition of the sample, numbers of capillaries formed around the aorta were counted. The results are shown in Table 2. The $IC_{50}$ value of each sample is defined as a concentration that the number of blood capillaries is 50% of that observed when no sample was added.

TABLE 2

| VD1207 | $IC_{50}$ (µg/ml) |
|---|---|
| A2 | 1 |
| B | 0.053 |
| C | 0.050 |
| D | 0.019 |
| E | 0.047 |
| F | 0.067 |
| F' | 0.10 |
| G1 | 0.070 |
| G2 | 0.034 |
| G' | 0.11 |
| H | 0.38 |

Example 13

Inhibitory Effect of Growth of Endothelial Cells

Endothelial cells derived from human umbilical vein (HUVEC; manufactured by Sanko Junyaku) incubated in an EGM medium (manufactured by Sanko Junyaku) were adjusted to $1\times10^4$ cells/ml and each 100 µl were separately placed on a 96-well plate. After incubating overnight, 100 µl of medium containing sample were added thereto followed by incubating for three days. The cell numbers at that time were measured by MTT method. That is, 50 µl of PBS solution containing 0.33% of 3-(4,5-dimethylthiazol-2-yl)-2,5-diphenyltetrazolium bromide (MTT) was added thereto and incubation was continued for further 3–4 hours. After the supernatant liquid of the culture was removed, 100 µl of DMSO was added to dissolve a formazane which was formed in the cells and the absorbance at the wave length of 460 nm was measured by use of plate reader. The results are shown in Table 3. The $IC_{50}$ value is defined as a concentration that the absorbance was 50% of that observed when no sample was added.

TABLE 3

| VD1207 | $IC_{50}$ (µg/ml) |
|---|---|
| A1 | 17.6 |
| A2 | 18.7 |
| B | 0.24 |
| C | 0.08 |
| D | 0.18 |
| E | 0.21 |
| F | 0.06 |
| G1 | 0.11 |

TABLE 3-continued

| VD1207 | IC$_{50}$ (μg/ml) |
|---|---|
| G2 | 0.07 |
| H | 0.52 |
| U1 | 6.5 |
| U2 | 7.1 |

Example 14

Effect of Inhibiting the Expression of an Adhesion Molecules on Endothelial Cells Endothelial cells derived from human umbilical vein (HUVEC) were cultured on a 96-well plate until they were fallen in a confluent state. The culture broth was removed. After 150 μl of a new culture broth was added to each well, 20 μl of a sample solution was added thereto. After 15 minutes, 30 μl of TNFα was added such that the final concentration became 1 ng/ml and it was incubated at 37° C. for 4 hours in a 5% CO$_2$ incubator. Next, the culture broth was removed and the cells were washed twice with a phosphate buffer (PBS). Further, a PBS solution containing 0.025% glutaraldehyde was added and the well was allowed to stand at room temperature for 6 minutes to fix the cells. After the cells were immobilized, they were washed twice with 200 μl of phosphate buffer (PBSA) containing 0.25% BSA. Thereafter 100 μl of a PBSA solution containing 1 μg/ml of mouse anti-human VCAM-1 (R&D systems) or a mouse anti-human E-selectin antibody (R&D systems) was added to each well. The well was allowed to stand at room temperature for 30 minutes and then the cells were again washed. A PBSA solution containing 100 μl of peroxidase-conjugated goat anti-mouse antibody (Cosmo Bio Co., Ltd.) was added to the well. Then the well was allowed to stand at room temperature for 30 minutes and thereafter the cells were washed. In succession, 100 μl of 3,3*,5,5*-tetramethylbenzyidine (TMB) substrate solution was added to develop a color. Next, the coloring was stopped by 100 μl of 1M phosphoric acid to measure the absorbance at 450 nm. Table 4 shows the value of IC$_{50}$ of each sample, which is defined as a concentration that the absorbance was 50% of that observed when cells were stimulated with TNFA.

TABLE 4

| Compound | VCAM-1 (μg/ml) | E-select (μg/ml) |
|---|---|---|
| VD1207 B | 2.48 | 4.0 |
| C | 0.85 | 1.23 |
| D | 1.11 | 1.40 |
| E | 2.59 | 4.44 |
| F | <0.63 | 0.84 |
| H | 1.06 | 2.48 |

Example 15

Antiangiogenic Effect of VD1207C in vivo

Whether angiogenesis induced by human colorectal cancer (WiDr cells) was inhibited by administering VD1207C or not was studied to examine the antiangiogenic effect of VD1207C in vivo.

Figure 1:
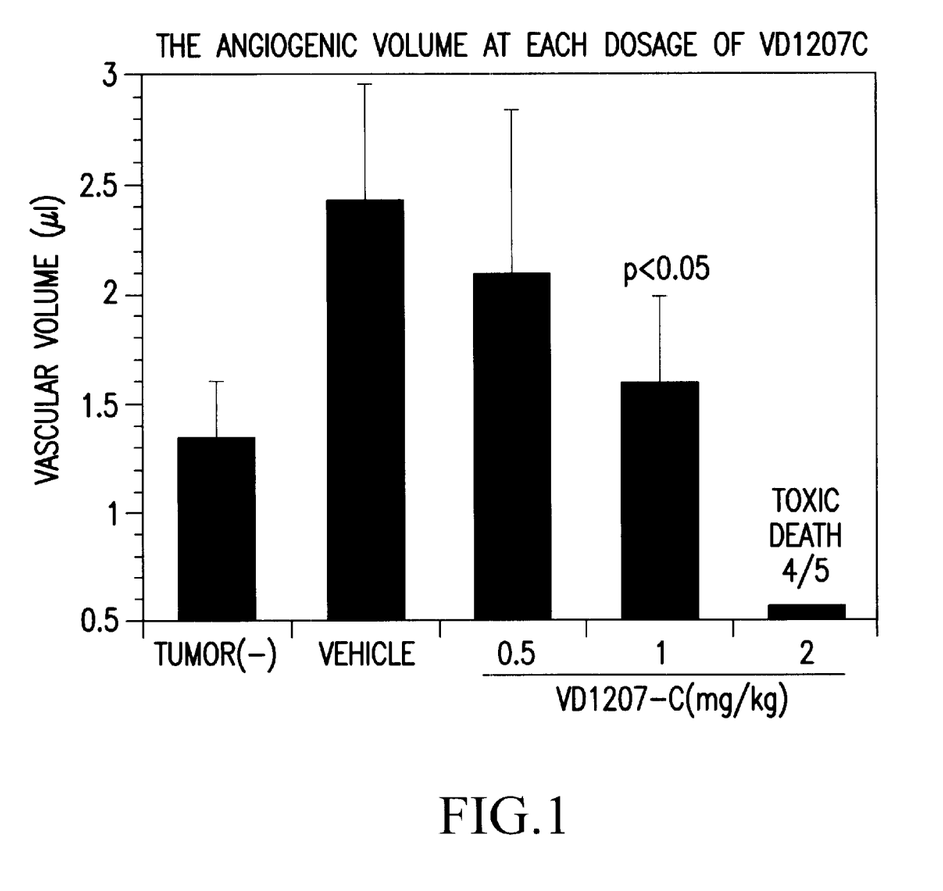
FIG. 1 shows angiogenic vascular volume at each dosage of VD1207C.

A chamber in which the WiDr cells were sealed was transplanted to a mouse. Then VD1207C was administered intraperitoneally at each dose of 0.5, 1.0 and 2.0 mg/kg for 4 days once a day. The amount of angiogenesis induced by the tumor was measured quantitatively by measuring the radiao activity in the skin touching with the chamber as the amount of blood by statically injecting erythrocytes labeled by $^{51}$Cr. In FIG. 1, vascular volume generated at each dose of VD1207C is shown. Angiogenesis induced by WiDr cells was inhibited with a significant difference by administering VD1207C at a dose of 1 mg/kg. It is clear from this result that VD1207C has an antiangiogenic effect even in vivo.

Example 16

Anti-metastatic Effect of VD1207C

Based on the fact that VD1207C had an antiangiogenic effect even in vivo, whether or not the hepatic metastasis of mouse colon cancer (Colon 38-OT-7) was inhibited by the administration of VD1207C was examined.

The mouse colon cancer (Colon 38-OT-7) having a high incidence of the hepatic metastasis was transplanted to the mouse caecum. Then VD1207C was administered intraperitoneallyat each dose of 0.5, 1.0 and 2.0 mg/kg once a day since 12 days after the transplantation. Table 5 shows the number of hepatic metastatic nodules at each dose of VD1207C. VD1207C decreased the number of the metastatic nodules at a dose ranging from 0.5 mg/kg and no metastatic nodules was observed at all at a dose of 2.0 mg/kg. From these results, it is clarified that VD1207C has an effect of inhibiting the metastasis of cancer.

TABLE 5

| | | | | Hepatic metastasis | | |
|---|---|---|---|---|---|---|
| Drugs | Dose (mg/kg) | n | Toxic death | No. of metastaticnodules | | Incidence |
| | | | | (mean ± STD) | median | |
| Vehicle | — | 8 | — | 2,6,10,17,21,29,41,63 (23.6 ± 20.3) | 19.0 | 8/8 |
| VD1207C | 0.5 | 8 | 1 | 0,0,0,1,16,25,26 (9.7 ± 12.2) | 1.0 | 5/7 |
| | 1.0 | 8 | 2 | 0,0,0,1,2,4 (1.2 ± 1.6) | 0.5 | 3/6 |
| | 2.0 | 8 | 3 | 0,0,0,0,0 | 0 | 0/5 |

Example 17

Safety of VD1207 Analogues

Each of VD1207B, C, D, E, F and G2 was continuously administered intraperitoneally at each dose of 1 mg/kg and 2 mg/kg over 4 days to examine the safety of VD1207 analogues.

Figure 2A:
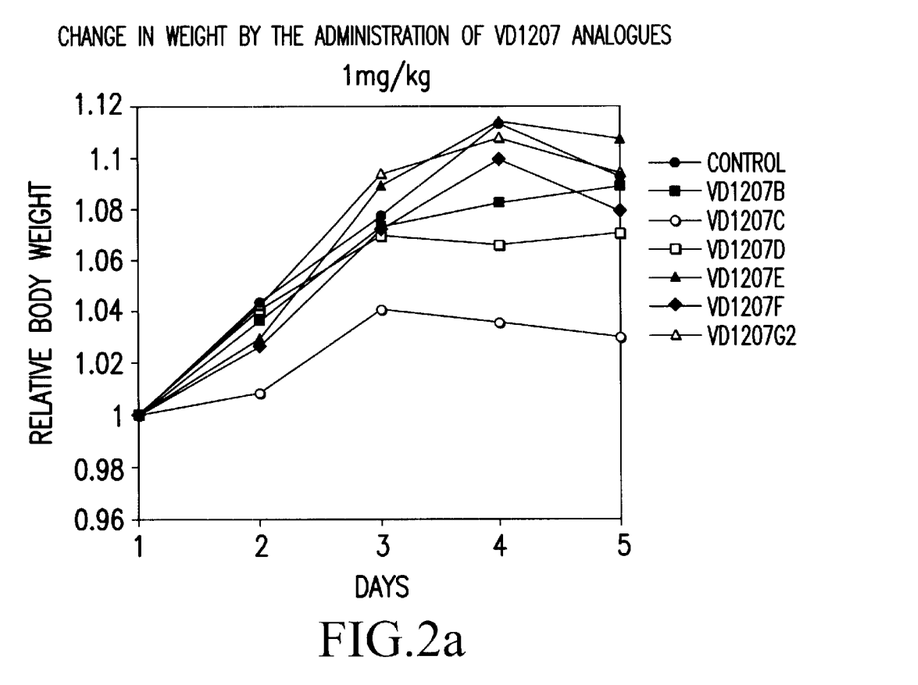
FIGS. 2a and 2b show a change in weight when each of VD1207B, C, D, E, F and G2 was continuously administered intraperitoneally at each dose of 1 mg/kg and 2 mg/kg for 4 days.
Figure 2B:
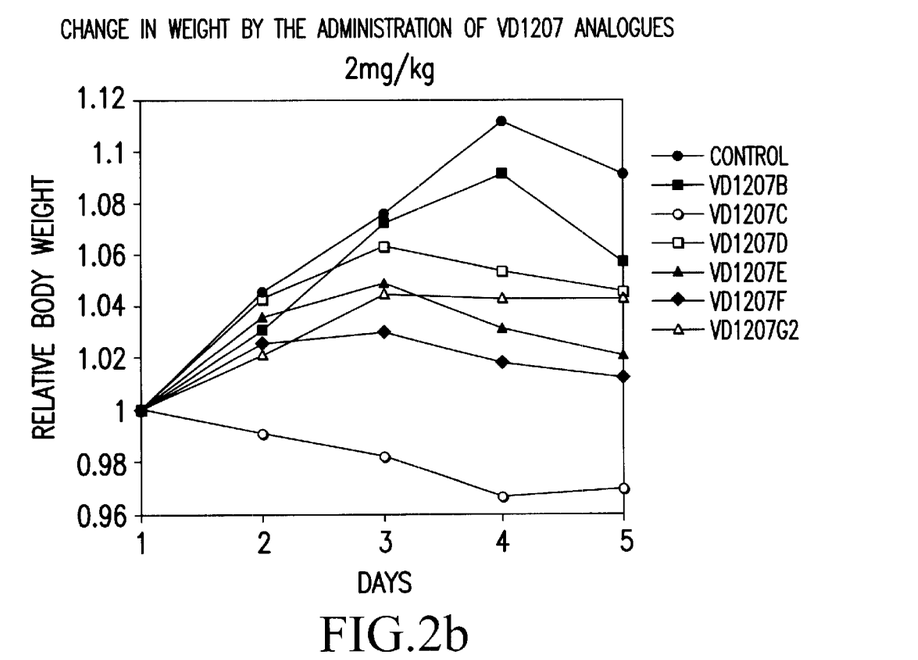

As a result, as shown in FIGS. 2a and 2b, inhibition to an increase in weight at a dose of 1 mg/kg and a reduction in weight at a dose of 2 mg/kg were observed in the case of VD1207C whereas no reduction in weight was observed in the case of other analogues. Also, as shown by autoptic findings of Table 6, an increase in the weight of each of the liver, kidney and lung were observed in the case of VD1207C and F whereas the toxicity of other analogues was low.

TABLE 6

| Examination | B | | C | | D | | E | | F | | G2 | |
|---|---|---|---|---|---|---|---|---|---|---|---|---|
| items | 1 | 2 | 1 | 2 | 1 | 2 | 1 | 2 | 1 | 2 | 1 | 2 |
| Body weight | — | — | — | ↓ | — | — | — | — | — | — | — | — |
| Feeds | NT | NT | NT | NT | NT | NT | NT | NT | NT | NT | NT | NT |
| Water | NT | NT | NT | NT | NT | NT | NT | NT | NT | NT | NT | NT |

TABLE 6-continued

| Examination items | B 1 | B 2 | C 1 | C 2 | D 1 | D 2 | E 1 | E 2 | F 1 | F 2 | G2 1 | G2 2 |
|---|---|---|---|---|---|---|---|---|---|---|---|---|
| Blood | | | | | | | | | | | | |
| (RBC) | — | — | — | — | — | — | — | — | — | — | — | — |
| (WBC) | — | — | — | — | — | — | ↓ | — | ↓ | — | — | ↓ |
| (PLAT) | — | — | — | ↓ | — | — | — | — | — | — | — | — |
| Biochemistry | | | | | | | | | | | | |
| (UN) | — | — | — | — | — | — | — | — | — | — | — | — |
| (GPT) | — | — | — | — | — | — | — | — | — | — | — | — |
| Weight | | | | | | | | | | | | |
| (liver) | ↑ | ↑ | ↑ | ↑ | ↑ | ↑ | ↑ | ↑ | ↑ | ↑ | ↑ | ↑ |
| (kidney) | — | — | ↑ | ↑ | — | — | — | — | — | ↑ | ↑ | — |
| (lung) | — | — | ↑ | ↑ | — | — | — | — | — | ↑ | — | — |
| (spleen) | — | — | — | — | — | — | — | — | — | — | — | — |
| Pathology | NT | NT | NT | NT | NT | NT | NT | NT | NT | NT | NT | NT |

In the table, "NT" indicates that the measurement was not made, "-" indicates no abnormality and "↑" and "↓" indicate an increase and a decrease, respectively.

What is claimed is:

1. A chemical compound selected from a group consisting of the following compounds:

(1)

(2)

(3)

(4), (5), (6), (7), (8), and

-continued (9)

wherein (1) and (2) are epimers at * and (7) and (8) are epimers at *.

2. A pharmaceutical composition, comprising a pharmacologically effective amount of the compound according to claim 1, a pharmaceutically acceptable salt thereof or a hydrate thereof, and a pharmacologically acceptable carrier.

* * * * *